United States Patent
Maeda et al.

(10) Patent No.: US 9,052,277 B2
(45) Date of Patent: Jun. 9, 2015

(54) IMAGE CAPTURING APPARATUS, IMAGE CAPTURING METHOD, AND COMPUTER READABLE MEDIUM

(75) Inventors: Kiyohiro Maeda, Kanagawa (JP); Hiroshi Yamaguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 626 days.

(21) Appl. No.: 12/413,037

(22) Filed: Mar. 27, 2009

(65) Prior Publication Data

US 2009/0247881 A1    Oct. 1, 2009

(30) Foreign Application Priority Data

Mar. 27, 2008 (JP) ................................. 2008-084924
Jan. 14, 2009 (JP) ................................. 2009-005854

(51) Int. Cl.
*A61B 6/00* (2006.01)
*A61B 1/04* (2006.01)
*A61B 1/06* (2006.01)
*G01N 21/31* (2006.01)
(Continued)

(52) U.S. Cl.
CPC .............. *G01N 21/314* (2013.01); *A61B 1/0638* (2013.01); *A61B 1/0653* (2013.01); *A61B 5/0059* (2013.01); *A61B 5/1075* (2013.01); *A61B 5/14551* (2013.01); *A61B 5/441* (2013.01); *A61B 5/489* (2013.01); *G01N 2021/1776* (2013.01); *A61B 1/063* (2013.01); *A61B 1/0646* (2013.01)

(58) Field of Classification Search
CPC .. A61B 1/0638; A61B 1/0646; A61B 1/0653; A61B 5/0059; A61B 5/441; A61B 5/489; G01N 21/314

USPC .......................................... 600/101, 109, 160
See application file for complete search history.

(56) References Cited

U.S. PATENT DOCUMENTS 7,187,810 B2 * 3/2007 Clune et al. .................... 382/294
7,667,180 B2 * 2/2010 Maeda ......................... 250/208.1
(Continued)

FOREIGN PATENT DOCUMENTS

JP     5014738 A    1/1993
JP     10-225436 A  8/1998
(Continued)

OTHER PUBLICATIONS

EP Communication, dated Aug. 14, 2009, issued in corresponding EP Application No. 09004500.6, 10 pages.
(Continued)

*Primary Examiner* — Katherine Fernandez
(74) *Attorney, Agent, or Firm* — Sughrue Mion, PLLC

(57) ABSTRACT

Provided is an image capturing apparatus comprising a light emitting section that emits light to a subject; a light receiving section that receives light in a first wavelength region and light in a second wavelength region from the subject, the second wavelength region being different from the first wavelength region; a reflectance calculating section that calculates a first reflectance of light in the first wavelength region from the subject and a second reflectance of light in the second wavelength region from the subject, based on the light emitted by the light emitting section and the light received by the light receiving section; and a depth identifying section that calculates a depth, from a surface of the subject, of an object inside the subject that is included in an image resulting from the light received by the light receiving section, based on the first reflectance and the second reflectance.

11 Claims, 15 Drawing Sheets

(51) Int. Cl.
*A61B 5/00* (2006.01)
*A61B 5/107* (2006.01)
*A61B 5/1455* (2006.01)
*G01N 21/17* (2006.01)

(56) References Cited

U.S. PATENT DOCUMENTS

| | | | |
|---|---|---|---|
| 7,873,407 B2* | 1/2011 | Levenson et al. | 600/476 |
| 2001/0056237 A1* | 12/2001 | Cane et al. | 600/475 |
| 2006/0276966 A1* | 12/2006 | Cotton et al. | 702/1 |

FOREIGN PATENT DOCUMENTS

| | | |
|---|---|---|
| JP | 2002-027244 A | 1/2002 |
| JP | 2002-034893 A | 2/2002 |
| JP | 2002-034908 A | 2/2002 |
| JP | 2002-95635 A | 4/2002 |
| JP | 2003501651 A | 1/2003 |
| JP | 2004033451 A | 2/2004 |
| JP | 2006-326153 A | 12/2006 |
| WO | 01/63251 A1 | 8/2001 |
| WO | 2005/070290 A1 | 8/2005 |

OTHER PUBLICATIONS

Communication pursuant to Article 94(3) EPC, dated Aug. 23, 2011, issued in corresponding EP Application No. 09 004 500.6, 8 pages.

Notification of Reasons for Refusal, dated Feb. 5, 2013, issued in corresponding JP Application No. 2009-005854, 9 pages in English and Japanese.

* cited by examiner

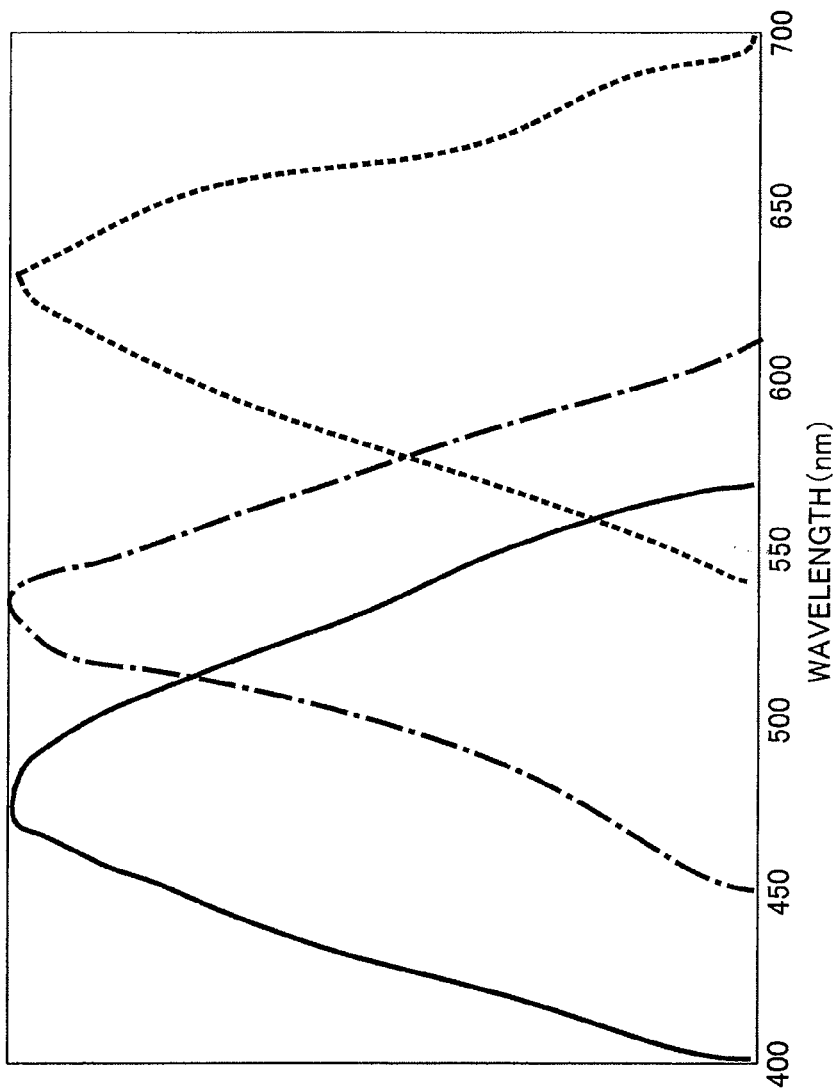
F I G . 3

F I G . 7

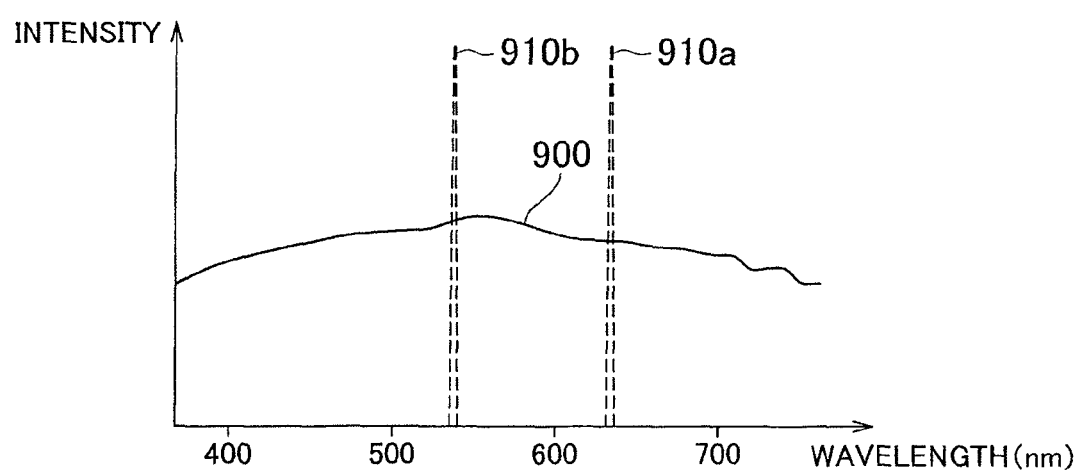
F I G . 9

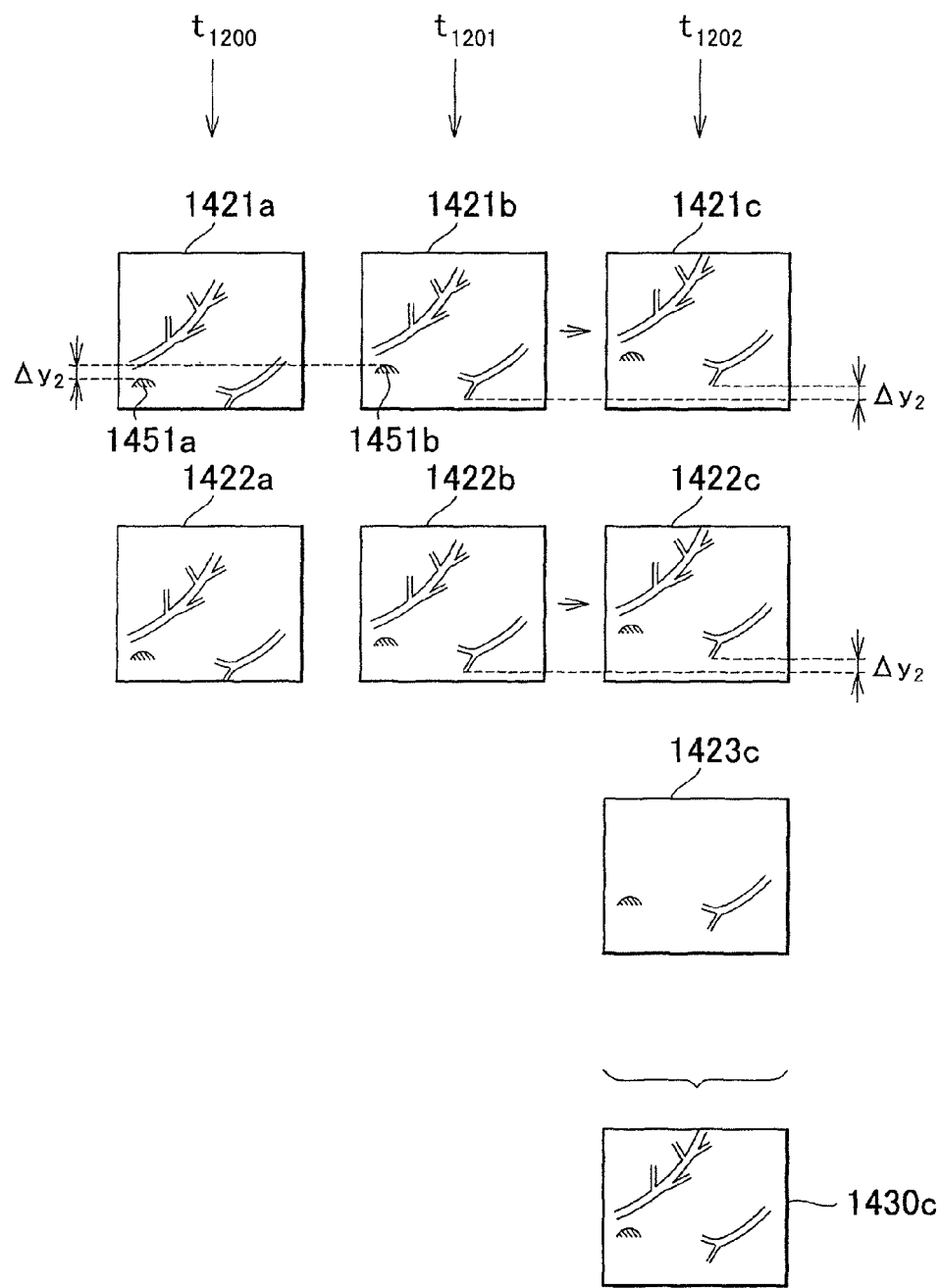
F I G. 13

IMAGE CAPTURING APPARATUS, IMAGE CAPTURING METHOD, AND COMPUTER READABLE MEDIUM

CROSS REFERENCE TO RELATED APPLICATION

The present application claims priority from Japanese Patent Applications No. 2008-084924 filed on Mar. 27, 2008, and No. 2009-005854 filed on Jan. 14, 2009, the contents of which are incorporated herein by reference.

BACKGROUND

1. Technical Field

The present invention relates to an image capturing apparatus that captures an image, an image capturing method, and a computer readable medium storing thereon a program. In particular, the present invention relates to an image capturing apparatus, an image capturing method, and a computer readable medium storing thereon a program for identifying the depth of an object inside a subject.

2. Related Art

A technique is known for viewing organic information near a surface of a living organism by controlling the wavelength region of light irradiating a subject, as disclosed, for example, in Japanese Patent Application Publications No. 2002-95635, No. 2002-34893, and No. 2002-34908.

Furthermore, a technique is known for detecting a lesion in an organism based on a fluorescent light component in a short wavelength region and a fluorescent light component in a long wavelength region extracted from an autofluorescent component emitted by the organism, as in, for example, Japanese Patent Application Publication No. 10-225436. Furthermore, a technique for generating an image indicating an oxidized hemoglobin distribution by calculating a difference between two images resulting from different wavelength regions is known as in, for example, Japanese Patent Application Publications No. 2002-272744 and No. 2006-326153.

The above techniques, however, cannot measure the depth of a blood vessel from the surface of the organism. For example, when using a technique that measures the depth of the blood vessel based on the amount of light reflected from the organism, this measurement is affected by the texture of the surface of the organism and changes in the amount of light due to movement of the light source or the like, so that a stable measurement result cannot be obtained.

SUMMARY

Therefore, it is an object of an aspect of the innovations herein to provide an image capturing apparatus, an image capturing method, and a computer readable medium, which are capable of overcoming the above drawbacks accompanying the related art. The above and other objects can be achieved by combinations described in the independent claims. The dependent claims define further advantageous and exemplary combinations of the innovations herein.

According to a first aspect related to the innovations herein, one exemplary image capturing apparatus may comprise a light emitting section that emits light to a subject; a light receiving section that receives light in a first wavelength region and light in a second wavelength region from the subject, the second wavelength region being different from the first wavelength region; a reflectance calculating section that calculates a first reflectance of light in the first wavelength region from the subject and a second reflectance of light in the second wavelength region from the subject, based on the light emitted by the light emitting section and the light received by the light receiving section; and a depth identifying section that calculates a depth, from a surface of the subject, of an object inside the subject that is included in an image resulting from the light received by the light receiving section, based on the first reflectance and the second reflectance.

According to a second aspect related to the innovations herein, one exemplary image capturing method may comprise providing a light emitting section that emits light to a subject; providing a light receiving section that receives light in a first wavelength region and light in a second wavelength region from the subject, the second wavelength region being different from the first wavelength region; calculating a first reflectance of light in the first wavelength region from the subject and a second reflectance of light in the second wavelength region from the subject, based on the light emitted by the light emitting section and the light received by the light receiving section; and calculating a depth, from a surface of the subject, of an object inside the subject that is included in an image resulting from the light received by the light receiving section, based on the first reflectance and the second reflectance.

According to a third aspect related to the innovations herein, one exemplary computer readable medium may include a computer readable medium storing thereon a program for use by an image capturing apparatus. The image capturing apparatus may include a light emitting section that emits light to a subject; and a light receiving section that receives light in a first wavelength region and light in a second wavelength region from the subject, the second wavelength region being different from the first wavelength region. The program may cause the image capturing apparatus to function as a reflectance calculating section that calculates a first reflectance of light in the first wavelength region from the subject and a second reflectance of light in the second wavelength region from the subject, based on the light emitted by the light emitting section and the light received by the light receiving section; and a depth identifying section that calculates a depth, from a surface of the subject, of an object inside the subject that is included in an image resulting from the light received by the light receiving section, based on the first reflectance and the second reflectance.

The summary clause does not necessarily describe all necessary features of the embodiments of the present invention. The present invention may also be a sub-combination of the features described above. The above and other features and advantages of the present invention will become more apparent from the following description of the embodiments taken in conjunction with the accompanying drawings.

BRIEF DESCRIPTION OF THE DRAWINGS

FIG. 3 shows exemplary light receiving characteristics of the light receiving elements in the light receiving section 130.

FIG. 7 shows an exemplary display of the display section 150.

FIG. 9 shows an exemplary spectrum of light emitted by the light emitting section 114 to irradiate the subject.

FIG. 13 shows another example of the generation of a subject frame image in which the movement is corrected.

DESCRIPTION OF EXEMPLARY EMBODIMENTS

Hereinafter, some embodiments of the present invention will be described. The embodiments do not limit the invention according to the claims, and all the combinations of the features described in the embodiments are not necessarily essential to means provided by aspects of the invention.

Figure 1:
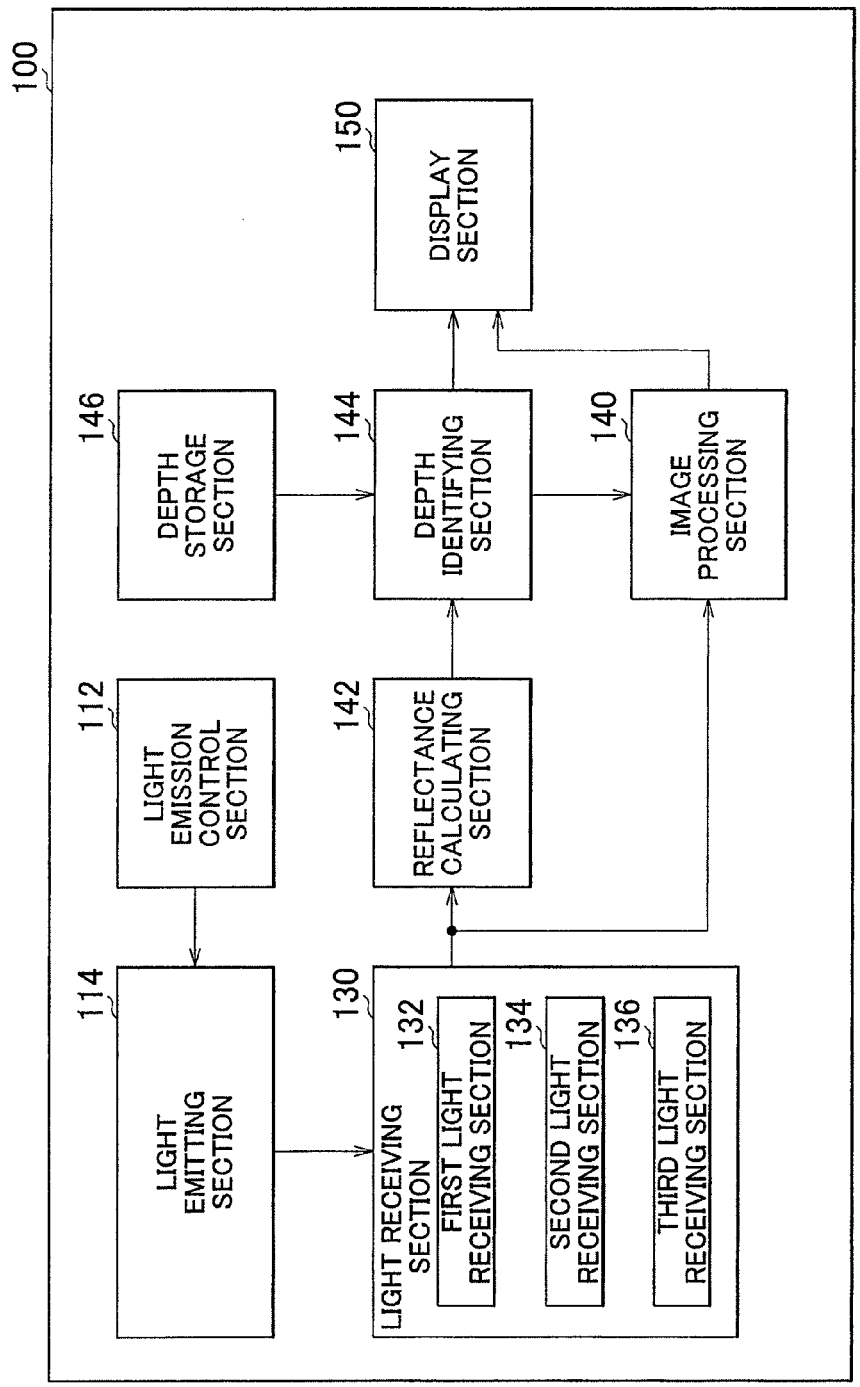
FIG. 1 shows an exemplary block configuration of an image capturing apparatus 100 according to an embodiment of the present invention.

FIG. 1 shows an exemplary block configuration of an image capturing apparatus 100 according to an embodiment of the present invention. The image capturing apparatus 100 includes a light emission control section 112, a light emitting section 114, a light receiving section 130, a reflectance calculating section 142, a depth identifying section 144, a depth storage section 146, an image processing section 140, and a display section 150.

The image capturing apparatus 100 may be an endoscope. If the image capturing apparatus 100 is an endoscope, the light emitting section 114 and the light receiving section 130 may be provided at a tip of the portion of the endoscope that is inserted into an organism. As another example, the light emitting section 114 may be disposed outside of the inserted portion and irradiate the organism with light via a light guide provided on the inserted portion of the endoscope. The light receiving section 130 may be provided outside of the inserted portion and receive light from the organism via the light guide provided on the inserted portion of the endoscope.

The light emitting section 114 emits light to a subject. For example, the light emitting section 114 emits light that includes light in a first wavelength region and light in a second wavelength region. The light in the first wavelength region may be red light, i.e. a wavelength range of 600 nm to 750 nm, and the light in the second wavelength region may be green light, i.e. a wavelength range of 490 nm to 600 nm.

The light emitting section 114 may emit light that further includes light in a third wavelength region. The light in the third wavelength region may be blue light, i.e. a wavelength range of 400 nm to 490 nm. The light emitting section 114 emit white light as the light that includes light in the first wavelength region and light in the second wavelength region.

As another example, the light emitting section 114 may sequentially emit light in the first wavelength region and light in the second wavelength region. In this case, the light emitting section 114 may sequentially emit light in the red light wavelength region and light in the green light wavelength region, for example. The light emitting section 114 may include a first light emitting element that emits light in the first wavelength region and a second light emitting element that emits light in the second wavelength region. The light emitting section 114 may include a first light emitting filter that passes mainly light in the first wavelength region and a second light emitting filter that passes mainly light in the second wavelength region.

The light emitting section 114 may further sequentially emit light in the third wavelength region. For example, the light emitting section 114 may further sequentially emit light in the blue light wavelength region. The light emitting section 114 may further include a third light emitting element that emits light in the third wavelength region. The light emitting section 114 may further include a third light emitting filter that mainly passes light in the third wavelength region.

The light emission control section 112 controls the emission of light in the first wavelength region and light in the second wavelength region by the light emitting section 114. The light emission control section 112 may control the emission of light in the first wavelength region and light in the second wavelength region by the light emitting section 114 by controlling the first light emitting element and the second light emitting element. The light emission control section 112 may control the emission of light in the first wavelength region and light in the second wavelength region by the light emitting section 114 by controlling the first light emitting filter and the second light emitting filter.

The light emission control section 112 may further control the emission of light in the third wavelength region by the light emitting section 114. The light emission control section 112 may further control the emission of light in the third wavelength region by the light emitting section 114 by controlling the third light emitting element. The light emission control section 112 may further control the emission of light in the third wavelength region by the light emitting section 114 by controlling the third light emitting filter.

The light receiving section 130 receives, from the subject, light in the first wavelength region and light in the second wavelength region, which is different from the first wavelength region. More specifically, the light receiving section 130 receives light in the first wavelength region and light in the second wavelength region, these two wavelength regions having different degrees of dependency on the reflectance of the subject according to the distance of an object from the surface of the subject, that is, the depth of the object. For example, the light receiving section 130 receives light in the red light wavelength region from the subject as the light in the first wavelength region and receives light in the green light wavelength region from the subject as the light in the second wavelength region that is different from the light in the first wavelength region.

In the present embodiment, the light receiving section 130 includes a plurality of first light receiving elements 132 that receive light in the first wavelength region and a plurality of second light receiving elements 134 that receive light in the second wavelength region. The light receiving section 130 may include a plurality of first light receiving filters that pass mainly light in the first wavelength region and a plurality of second light receiving filters that pass mainly light in the second wavelength region, provided to correspond respectively to the plurality of first light receiving elements and the plurality of second light receiving elements.

In the present embodiment, the light receiving section 130 further includes a plurality of third light receiving elements 136 that receive light in the third wavelength region. The light receiving section 130 may also include a plurality of third light receiving filters that pass mainly light in the third wavelength region, provided to correspond to the plurality of third light receiving elements. The plurality of first light receiving elements 132, the plurality of second light receiving elements 134, and the plurality of third light receiving elements 136 may be arranged in an ordered manner on the light receiving section 130. The light receiving section 130 may also include corresponding pluralities of first light receiving filters, second light receiving filters, and third light receiving filters in the same ordered manner.

When the light emitting section 114 sequentially emits light in the first wavelength region and light in the second wavelength region, the light receiving section 130 may sequentially receive the light in the first wavelength region and the light in the second wavelength region. When the light emitting section 114 further sequentially emits light in the third wavelength region, the light receiving section 130 may further sequentially receive the light in the third wavelength region.

The first light receiving elements 132, the second light receiving elements 134, and the third light receiving elements 136 arranged in an ordered manner in the light receiving section 130 may be CCDs or CMOSs. As another example, the first light receiving elements 132, the second light receiving elements 134, and the third light receiving elements 136 arranged in an ordered manner in the light receiving section 130 may each be different CCDs or CMOSs.

The reflectance calculating section 142 calculates a first reflectance of light in the first wavelength region from the subject and a second reflectance of light in the second wavelength region from the subject, based on the light emitted by the light emitting section 114 and the light received by the light receiving section 130. For example, the reflectance calculating section 142 may calculate the first reflectance by dividing (i) the intensity of the light in the first wavelength region emitted by the light emitting section 114 by (ii) the intensity of the light in the first wavelength region received by the light receiving section 130, or vice-versa. The reflectance calculating section 142 may calculate the second reflectance by dividing (i) the intensity of the light in the second wavelength region emitted by the light emitting section 114 by (ii) the intensity of the light in the second wavelength region received by the light receiving section 130, or vice-versa.

The reflectance calculating section 142 may acquire, from the light emission control section 112, the amount of light in the first wavelength region and the amount of light in the second wavelength region emitted by the light emitting section 114. Instead, the reflectance calculating section 142 may acquire the amount of light in the first wavelength region and the amount of light in the second wavelength region emitted by the light emitting section 114 from a recording medium such as a memory on which this amount of light is stored in advance.

The reflectance calculating section 142 may calculate the first reflectance and the second reflectance for each partial region, where a partial region corresponds to a prescribed number of light receiving elements. For example, the reflectance calculating section 142 may calculate the first reflectance and the second reflectance for each partial region, where a partial region corresponds to a 2 by 2 pixel block, a 4 by 4 pixel block, or an 8 by 8 pixel block.

The reflectance calculating section 142 may calculate the first reflectance of each partial region as a total value or an average value of the first reflectance of each of the plurality of pixels in the partial region. In the same way, the reflectance calculating section 142 may calculate the second reflectance of each partial region as a total value or an average value of the second reflectance of each of the plurality of pixels in the partial region.

The reflectance calculating section 142 may calculate the first reflectance of a partial region by dividing (i) the total amount of light in the first wavelength region received by the plurality of pixels in the partial region by (ii) the amount of light in the first wavelength region emitted by the light emitting section 114. In the same way, the reflectance calculating section 142 may calculate the second reflectance of a partial region by dividing (i) the total amount of light in the second wavelength region received by the plurality of pixels in the partial region by (ii) the amount of light in the second wavelength region emitted by the light emitting section 114.

The reflectance calculating section 142 may calculate the first reflectance of a partial region by dividing (i) the total amount of light in the first wavelength region received by the plurality of pixels in the partial region by (ii) the amount of light in the partial region from among the light in the first wavelength region emitted by the light emitting section 114. In the same way, the reflectance calculating section 142 may calculate the second reflectance of a partial region by dividing (i) the total amount of light in the second wavelength region received by the plurality of pixels in the partial region by (ii) the amount of light in the partial region from among the light in the second wavelength region emitted by the light emitting section 114.

The depth identifying section 144 identifies the depth of an object inside the subject, which is the distance from the surface of the subject to the object included in an image resulting from the light received by the light receiving section 130, based on the first reflectance and the second reflectance calculated by the reflectance calculating section 142. For example, the depth identifying section 144 identifies a depth that is stored in the depth storage section 146 in association with a difference or ratio between the first reflectance and the second reflectance. When the reflectance calculating section 142 calculates the first reflectance and the second reflectance for each partial region, the depth identifying section 144 may identify the depth of the object in each partial region.

The depth storage section 146 stores in advance depth information indicating the depth at which an object exists inside the subject, in association with a difference or ratio between the reflectance of light in the first wavelength region from the subject and the reflectance of light in the second wavelength region from the subject.

The image processing section 140 performs image processing on the image resulting from the light received by the light receiving section 130 to generate a subject frame image, which includes an image of the object inside the subject. The subject frame image generated by the image processing section 140 is supplied to the display section 150 to be displayed. The image processing section 140 may perform image processing, on the subject frame image, that corresponds to the depth identified by the depth identifying section 144. The image processing according to depth may include color processing according to depth, such as coloring object images in the frame image according to depth, for example.

The display section 150 displays information concerning the depth identified by the depth identifying section 144. For example, the display section 150 displays this depth information simultaneously with the subject frame image. The display section 150 may display the subject frame image and the depth information in parallel. The display section 150 may display the depth information superimposed on the subject frame image.

The display section 150 may display the depth information simultaneously with a subject moving image that is a moving image including a plurality of subject frame images. The display section 150 may display the depth information and the subject moving image in parallel. The display section 150 may display the depth information superimposed on the subject moving image.

The display section 150 may display the depth information as text. The display section 150 may display the depth information as an image. For example, the display section 150 may show a color display of the subject frame image in which objects are colored according to depth.

Figure 2:
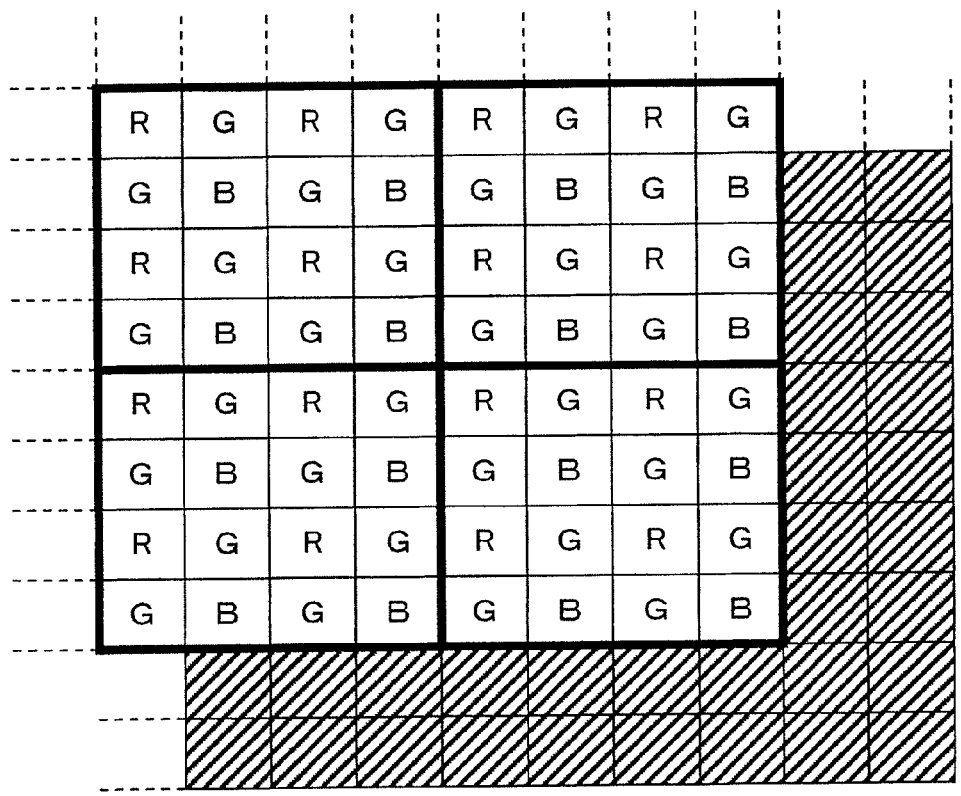
FIG. 2 shows an exemplary configuration of the light receiving elements and light receiving filters in the light receiving section 130.

FIG. 2 shows an exemplary configuration of the light receiving elements and light receiving filters in the light receiving section 130. The light receiving section 130 includes the plurality of first light receiving elements 132 that mainly receive light in the red light wavelength region, the plurality of second light receiving elements 134 that mainly receive light in the green light wavelength region, and the plurality of third light receiving elements 136 that mainly receive light in the blue light wavelength region.

In the light receiving section 130, the plurality of first light receiving elements 132, second light receiving elements 134, and third light receiving elements 136 are arranged at regular intervals. Furthermore, in the light receiving section 130, a plurality of first light receiving filters that mainly pass light in the red light wavelength region are arranged in front of the first light receiving elements 132, a plurality of second light receiving filters that mainly pass light in the green light wavelength region are arranged in front of the second light receiving elements 134, and a plurality of third light receiving filters that mainly pass light in the blue light wavelength region are arranged in front of the third light receiving elements 136.

The light receiving section 130 is partitioned into a plurality of partial regions. Each partial region includes a plurality of light receiving elements and a plurality of filters. In the example shown in FIG. 2, each partial region includes a 4 by 4 pixel block of light receiving elements and filters.

FIG. 3 shows exemplary light receiving characteristics of the light receiving elements in the light receiving section 130. The dotted line shows the light receiving characteristic of the first light receiving elements 132. For example, the first light receiving elements 132 are mainly sensitive to light in the first wavelength region mainly including light in the red light wavelength region, i.e. 600 nm to 750 nm.

The single-dash line shows the light receiving characteristic of the second light receiving elements 134. For example, the second light receiving elements 134 are mainly sensitive to light in the second wavelength region mainly including light in the green light wavelength region, i.e. 490 nm to 600 nm.

The solid line shows the light receiving characteristic of the third light receiving elements 136. For example, the third light receiving elements 136 are mainly sensitive to light in the third wavelength region mainly including light in the blue light wavelength region, i.e. 400 nm to 490 nm.

Figure 4:
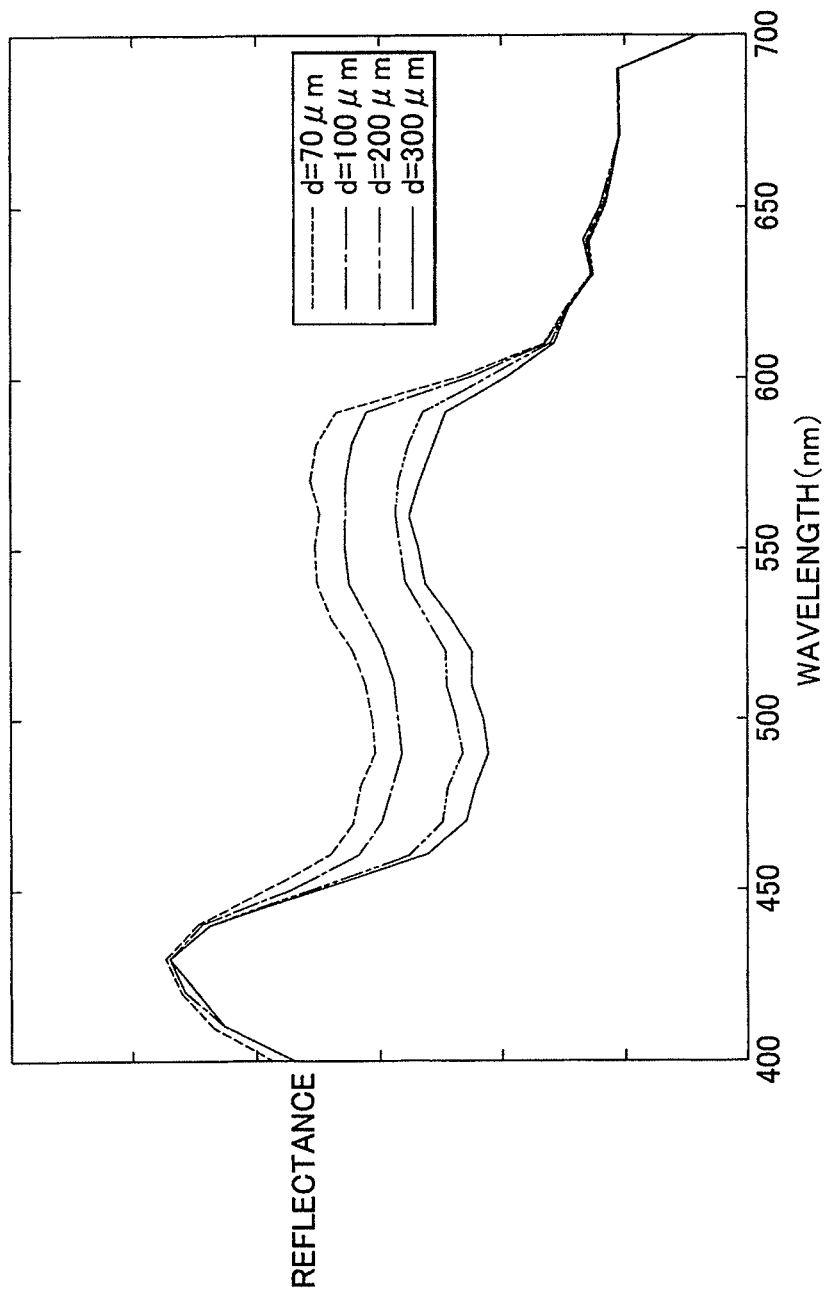
FIG. 4 shows exemplary reflective characteristics of the light from the subject.

FIG. 4 shows exemplary reflective characteristics of the light from the subject. In the graph of FIG. 4, the horizontal axis represents the wavelength of the light irradiating the organism, and the vertical axis represents the reflectance of the light from the organism.

The dotted line indicates the reflective characteristic of the light from the organism when the depth of the object, e.g. a blood vessel, in the organism is 70 μm from the surface of the organism. The single-dash line indicates the reflective characteristic of the light from the organism when the depth of a blood vessel in the organism is 100 μm from the surface of the organism.

The double-dash line indicates the reflective characteristic of the light from the organism when the depth of a blood vessel in the organism is 200 μm from the surface of the organism. The solid line indicates the reflective characteristic of the light from the organism when the depth of a blood vessel in the organism is 300 μm from the surface of the organism.

Figure 5:
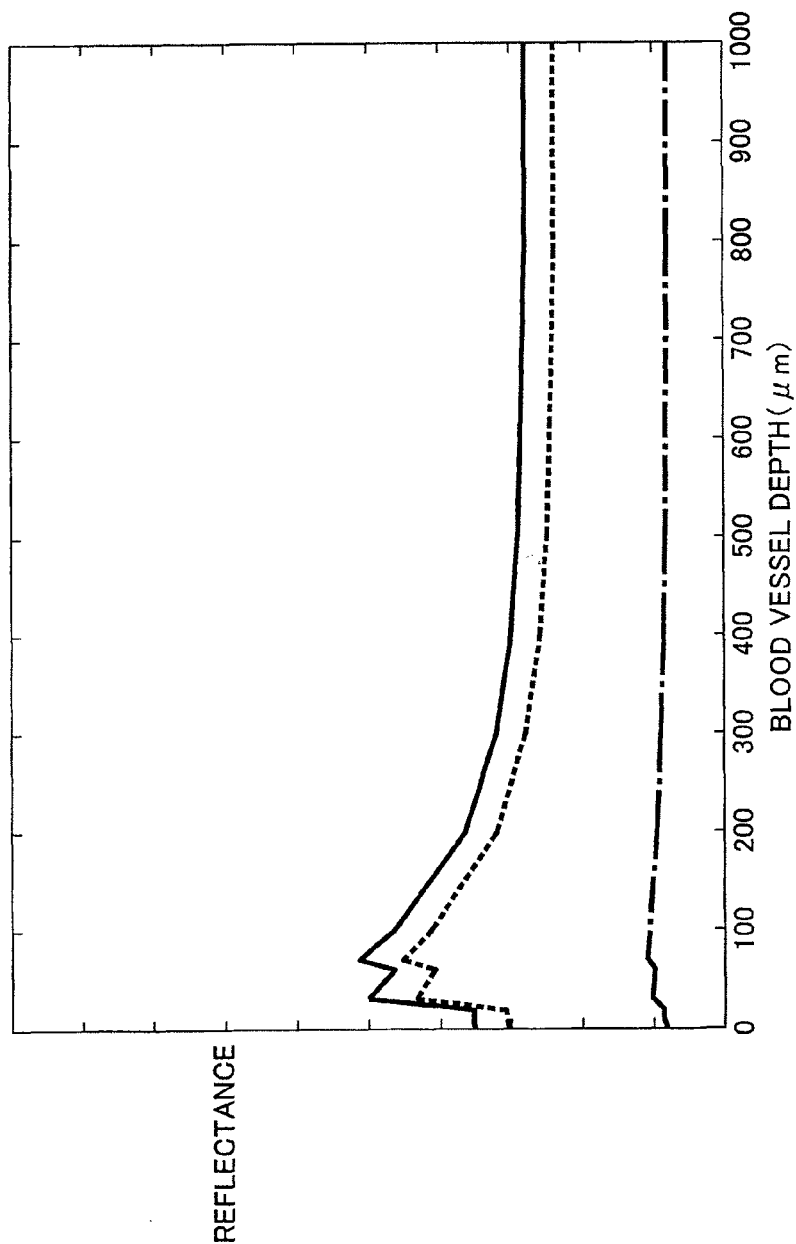
FIG. 5 shows another example of the reflective characteristics of the light from the subject.

FIG. 5 shows another example of the reflective characteristics of the light from the subject. In the graph of FIG. 5, the vertical axis represents the reflectance of the light from the organism, and the horizontal axis represents the depth of a blood vessel in an organism from the surface of the organism.

The single-dash line shows the reflective characteristic of light in the red light wavelength region, e.g. 600 nm to 700 nm. The dotted line shows the reflective characteristic of light in the green light wavelength region, e.g. 500 nm to 600 nm. The solid line shows the reflective characteristic of light in the blue light wavelength region, e.g. 400 nm to 500 nm.

As shown in FIGS. 4 and 5, in the red light wavelength region (600 nm to 700 nm), for example, the difference in the depth of the blood vessel inside the organism causes almost no difference in the reflective characteristics of the light from the organism. On the other hand, in the green light wavelength region (500 nm to 600 nm), the difference in the depth of the blood vessel inside the organism causes a large difference in the reflective characteristics of the light from the organism.

Therefore, after calculating the ratio between the reflectance of light in the green light wavelength region and the reflectance of light in the red light wavelength region, the image capturing apparatus 100 according to the present embodiment identifies the depth of the blood vessel based on the depth information stored in the depth storage section 146 and the calculated ratio. In this way, when measuring the depth of the blood vessel based on the amount of light reflected by the object, the image capturing apparatus 100 of the present embodiment can obtain a stable measurement result without being affected by a change in the amount of light irradiating the measurement target.

Figure 6:
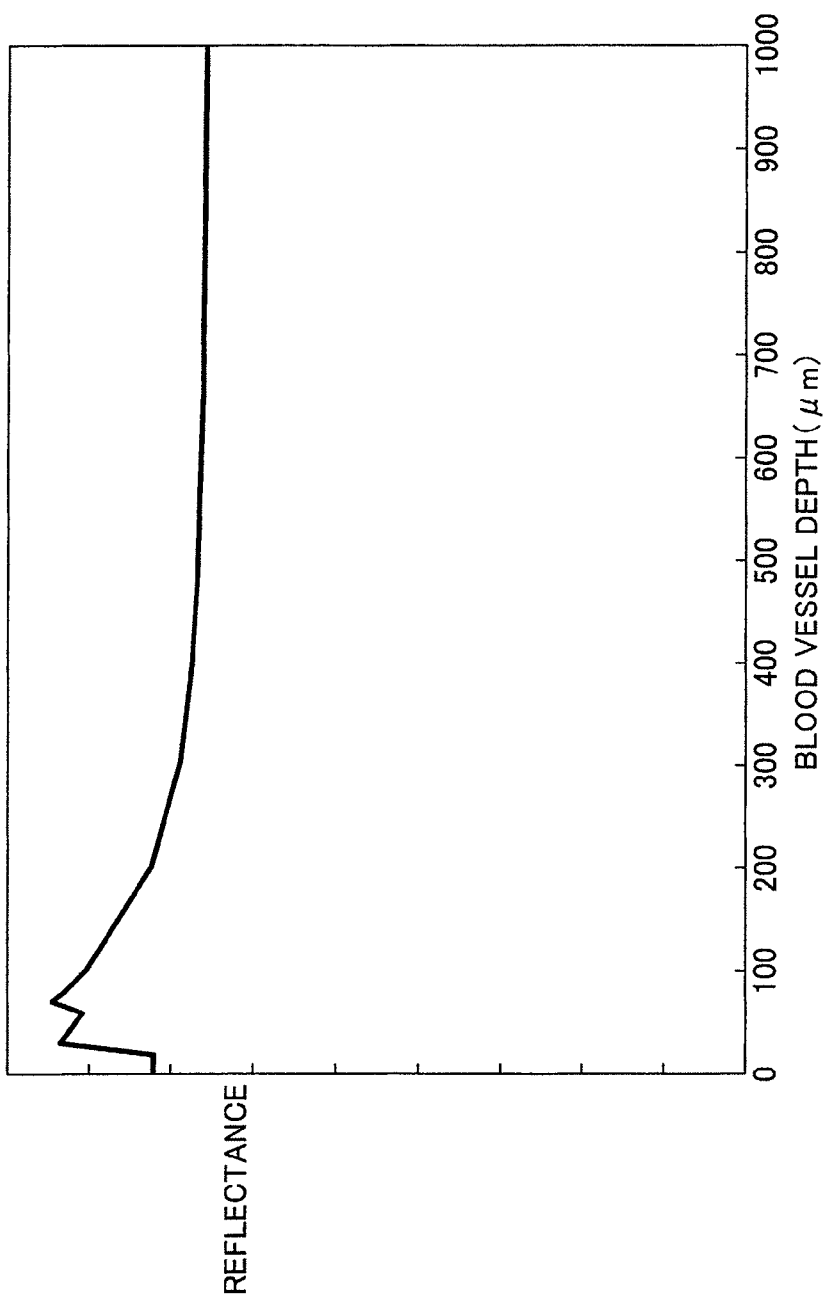
FIG. 6 shows an example of depth information stored in the depth storage section 146.

FIG. 6 shows an example of depth information stored in the depth storage section 146. In the graph of FIG. 6, the horizontal axis represents the depth of a blood vessel inside the subject, and the vertical axis represents a ratio between (i) the reflectance of light in the red light wavelength region from the subject and (ii) the reflectance of light in the green light wavelength region from the subject.

The depth identifying section 144 may calculate a ratio or a difference between the first reflectance and the second reflectance calculated by the reflectance calculating section 142. The depth identifying section 144 can then identify depth of the blood vessel based on the depth information stored in the depth storage section 146 and the calculated ratio or difference.

FIG. 7 shows an exemplary display of the display section 150. FIG. 7 shows a subject moving image acquired by capturing subject frame images of the organism and displayed by the display section 150.

The subject moving image includes a blood vessel, which is an example of the object inside the organism. The display section 150 may show a color display of the subject moving image in which the blood vessel is colored according to depth.

In this way, the image capturing apparatus 100 according to the present embodiment can measure the depth of an object inside an organism based on a difference or ratio between the reflectance of light in two wavelength regions having different amounts of change in the respective reflective characteristics of light due to a change in depth. Therefore, when measuring the depth of an object in an organism based on the amount of light reflected from the subject, the image capturing apparatus 100 of the present embodiment can obtain a stable measurement result without being affected by a change in the amount of light irradiating the measurement target.

Figure 8:
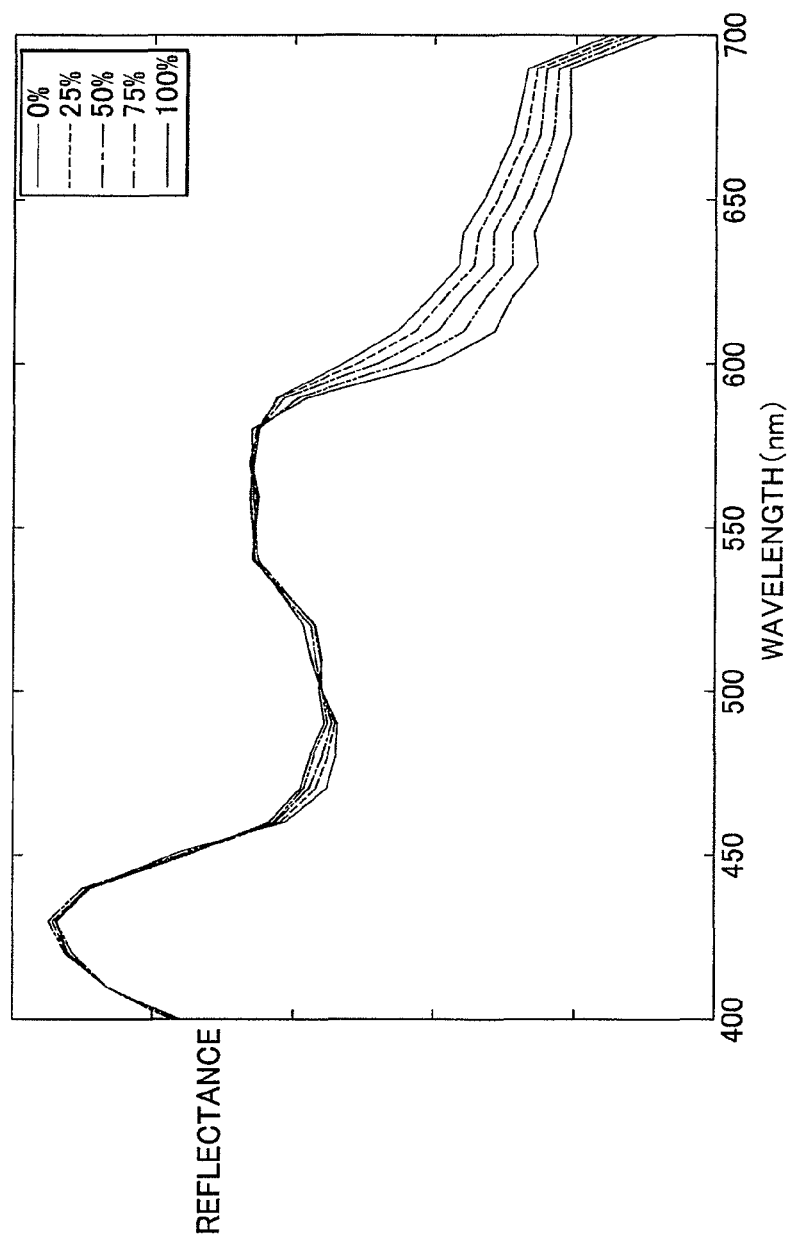
FIG. 8 shows another example of reflective characteristics of light from the subject.

FIG. 8 shows another example of reflective characteristics of light from the subject. In the graph of FIG. 8, the horizontal axis indicates the wavelength of light irradiating the organism, and the vertical axis represents the reflectance of light from the organism.

The dotted line shows the reflective characteristic of light from the organism when the hemoglobin oxygen saturation of the blood vessel is 25%. The single-dash line shows the reflective characteristic of light from the organism when the hemoglobin oxygen saturation of the blood vessel is 50%.

The double-dash line shows the reflective characteristic of light from the organism when the hemoglobin oxygen saturation of the blood vessel is 75%. The solid lines show the reflective characteristics of light from the organism when the hemoglobin oxygen saturation of the blood vessel is 0% and 100%.

In the green light wavelength region (500 nm to 600 nm), for example, the difference in the hemoglobin oxygen saturation causes almost no difference in the reflective characteristic of light from the subject. On the other hand, in the red light wavelength region (600 nm to 700 nm), for example, the difference in the hemoglobin oxygen saturation causes a large difference in the reflective characteristic of light from the subject Therefore, when the hemoglobin oxygen saturation of the blood vessel is the measurement target, both (i) the red light wavelength region dependent on a change in the measurement target and (ii) the green light wavelength region that is not dependent on a change in the measurement target are included in the reflective characteristic of the light from the organism. As a result, the depth storage section 146 can store, in advance, information indicating the hemoglobin oxygen saturation of the blood vessel in association with a difference or ratio between the reflectance of light in the green light wavelength region from the subject and the reflectance of light in the red light wavelength region from the subject.

The reflectance of light in the green light wavelength region and the reflectance of light in the red light wavelength region are then calculated. After calculating these two reflectances, the hemoglobin oxygen saturation of the blood vessel can be identified based on the calculated ratio and the information stored in the depth storage section 146. In this way, even when measuring the hemoglobin oxygen saturation of a blood vessel based on the amount of light reflected from the subject, the image capturing apparatus 100 of the present embodiment can obtain a stable measurement result without being affected by a change in the amount of light irradiating the measurement target.

FIG. 9 shows an exemplary spectrum of light emitted by the light emitting section 114 to irradiate the subject. The spectrum 900 is an example of a white light spectrum that includes light in the red light wavelength component, the green light wavelength region, and the blue light wavelength region. Irradiating the subject with this light results in a subject frame image that can be seen by the naked eye.

The depth storage section 146 may store, in advance, information indicating the depth of the object in association with a difference or ratio between (i) the reflectance of light in a relatively wide wavelength region that can be received by the second light receiving elements 134 and (ii) the reflectance of light in a relatively wide wavelength region that can be received by the first light receiving elements 132. The reflectance calculating section 142 may calculate (i) the reflectance of light in the relatively wide wavelength region that can be received by the second light receiving elements 134 and (ii) the reflectance of light in a relatively wide wavelength region that can be received by the first light receiving elements 132 based on the spectrum emitted by the light emitting section 114 and a signal from each of the first light receiving elements 132 and the second light receiving elements 134. In this way, the depth identifying section 144 can calculate the depth of the object by using white light to obtain a subject frame image that can be seen by the naked eye. In this case, the depth of the object can be calculated in real time.

In order to more accurately calculate the depth, it is desirable to irradiate the subject using light in a relatively narrow wavelength region as the light for measuring the depth. For example, the light emitting section 114 may emit light having the spectrum 910a as the light in the first wavelength region, and may emit light having the spectrum 910b as the light in the second wavelength region. The depth storage section 146 stores the information indicating the depth of an object, in association with a difference or ratio between the reflectance of light in a wavelength region corresponding to the spectrum 910b and the reflectance of light in a wavelength region corresponding to the spectrum 910a. The image capturing apparatus 100 can calculate the depth more accurately in this way than by calculating the depth based on the light in a relatively wide wavelength region.

The light emitting section 114 may irradiate the subject with light in a relatively narrow wavelength range corresponding to the spectrum 910a and the spectrum 910b by overlapping the white light, such as that shown by the spectrum 900, for obtaining the subject frame image to be viewable by the naked eye. If the intensity of the light in the relatively narrow wavelength region for measuring the depth is sufficiently high, the depth identifying section 144 can accurately calculate the depth using the depth stored in the depth storage section 146 in association with the difference or ratio between the reflectances of light in the relatively narrow wavelength regions. If the white light for measuring depth is overlapped when irradiating the subject, the intensity of the light in the relatively narrow wavelength regions can be increased by decreasing the intensity of the white light in the wavelength regions that can be received by the first light receiving elements 132 and the second light receiving elements 134.

The light emitting section 114 can emit white light (sometimes referred to hereinafter as "viewing light") for obtaining a subject frame image for viewing, and light in a relatively narrow wavelength region (sometimes referred to hereinafter as "measurement light") for measuring the depth. For example, the light emitting section 114 may include a xenon lamp as a light source of the viewing light and a semiconductor element such as an LED as the light source of the measurement light. When obtaining the subject frame image for viewing, the light emission control section 112 causes the xenon lamp to emit light but not the LED, so that the viewing light irradiates the subject. When measuring depth, the light emission control section 112 causes the LED to emit light but cuts the light emitted by the xenon lamp using a filter or the like, so that the subject is irradiated with the measurement light.

Figure 10:
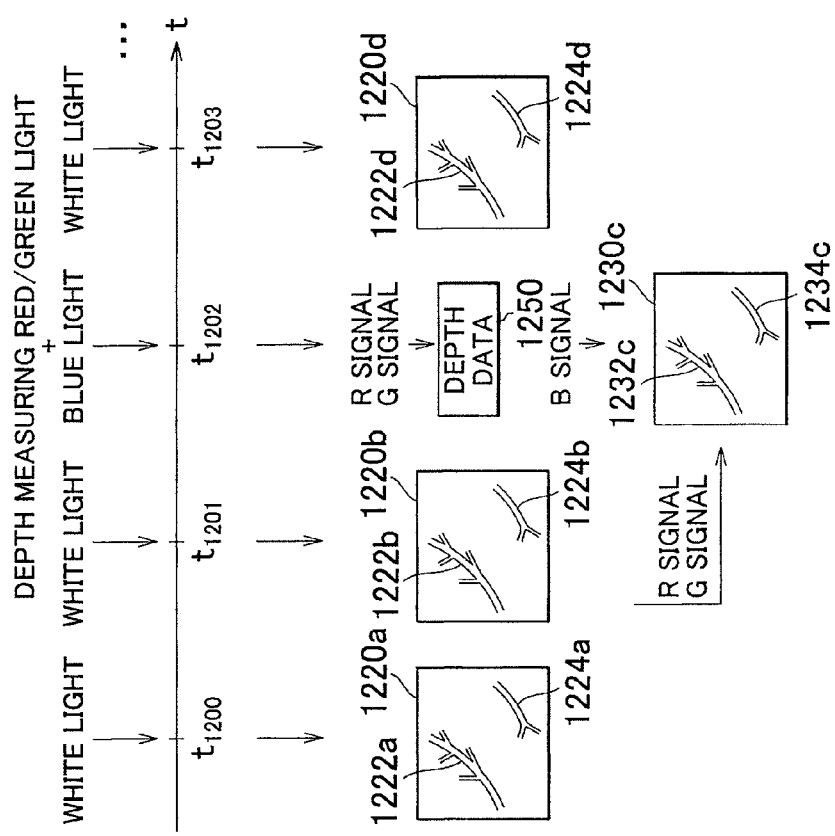
FIG. 10 shows the timing of the image capturing by the image capturing apparatus 100 and exemplary subject frame images.

FIG. 10 shows the timing of the image capturing by the image capturing apparatus 100 and exemplary subject frame images. The image capturing apparatus 100 captures subject frame images based on the light returning from the subject at times t1200, t1201, t1202, t1203, etc. The light emitting section 114 emits the viewing light to irradiate the subject at first timings that include t1200, t1201, and t1203.

The light receiving section 130 receives the radiated viewing light returning from the subject at the first timings. In this way, the image processing section 140 generates a subject frame image 1220a, a subject frame image 1220b, and a subject frame image 1220d based on the amount of light received by the light receiving elements at the first timings represented by t1200, t1201, and t1203, respectively. The display section 150 can then display the subject frame image 1220a, the subject frame image 1220b, and the subject frame image 1220d that are suitable for viewing. The subject frame image 1220a includes the blood vessel images 1222a and 1224a. The subject frame image 1220b includes the blood vessel images 1222b and 1224b. The subject frame image 1220d includes the blood vessel images 1222d and 1224d.

The light emitting section 114 emits measurement light to irradiate the subject at second timings including the time t1202. The light receiving section 130 receives the radiated measurement light returning from the subject at the second timings. The reflectance calculating section 142 calculates the respective reflectances from (i) a red signal from the first light receiving elements 132 at a second timing represented by t1202 and (ii) a green signal from the second light receiving elements 134 at a second timing represented by t1202. The depth identifying section 144 uses the calculated reflectances to calculate depth data 1250 indicating the depth of the blood vessel.

The image processing section 140 generates a subject frame image 1230c, which includes the blood vessel images 1232c and 1234c, based on the red signal from the plurality of first light receiving elements 132 at a first timing represented by t1201, the green signal from the plurality of second light receiving elements 134 at a first timing represented by t1201, and the blue signal from the plurality of third light receiving elements 136 at a second timing represented by t1202. The subject frame image 1230c can be treated as a subject frame image acquired using visible light at a second timing represented by t1202. The depth data 1250 can be used for image processing of the subject frame images 1230c, 1220d, and the like by the image processing section 140 or for the depth information displayed by the display section 150.

In this way, the image processing section 140 can generate a subject frame image from the viewing light, even at a timing when the measurement light irradiates the subject. The display section 150 can display a moving image without dropped frames by displaying the subject frame image 1220a, the subject frame image 1220b, the subject frame image 1230c, the subject frame image 1220d, etc. in series.

Figure 11:
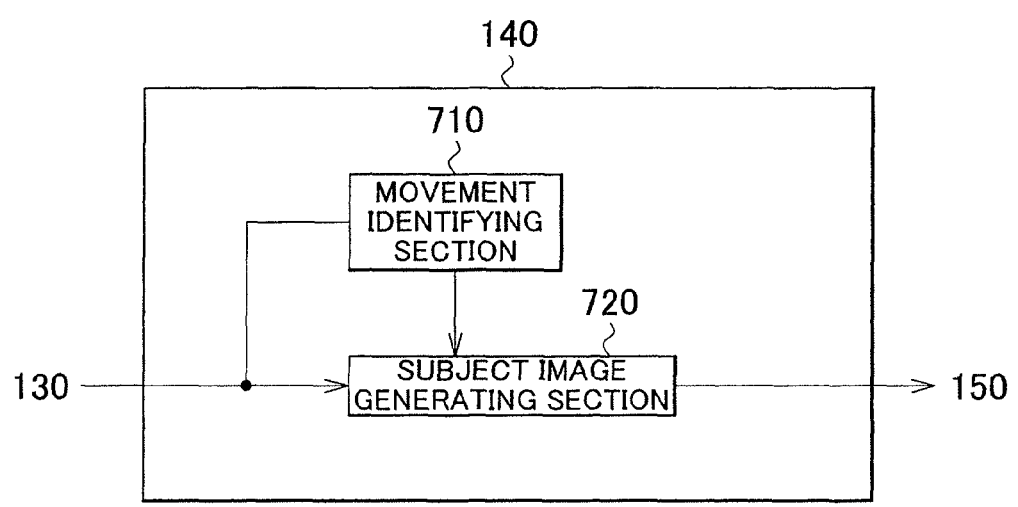
FIG. 11 shows an exemplary block configuration of the image processing section 140.

FIG. 11 shows an exemplary block configuration of the image processing section 140. For ease of explanation, FIG. 10 is used to describe an exemplary process of generating the subject frame image 1230c by multiplexing a red signal and a green signal at t1201 with a blue signal at t1202 when the movement of the image capturing apparatus 100, the movement of the subject, and the like do not cause a change over time in the captured image. However, in this process, a shift might arise between the red and green signals and the blue signal due to the movement of the image capturing apparatus 100, the movement of the subject, and the like.

The following Figures are used to describe the configuration of the image processing section 140 and the operation and function of the image processing section 140 for correcting the effect the movement mentioned above on the subject frame images. The image processing section 140 includes a movement identifying section 710 and a subject image generating section 720.

The movement identifying section 710 identifies movement of a subject image in a frame image, based on frame images created by blue signals at a plurality of timings. Here, the movement of the subject image refers to any movement that causes a change over time in the subject frame image, such as movement of the subject, movement of the image capturing apparatus 100, or a change over time in the zoom of the image capturing apparatus 100. The movement of the image capturing apparatus 100 includes a change over time in the image capturing position, and a change over time in the direction of the image capturing.

Using the light emission pattern described in relation to FIG. 10 as an example, the movement identifying section 710 identifies the movement based on frame images resulting from blue signals at the times t1201 and t1202. For example, the movement identifying section 710 identifies the positions of images of the same subject in a plurality of frame images using matching or the like, and then identifies the movement based on the difference between the identified positions.

The subject image generating section 720 corrects the red signal and the green signal at the time t1201 based on the identified movement, and generates the red signal and the green signal that are expected for the time t1202. The subject image generating section 720 multiplexes the corrected red signal and green signal with the blue signal at the time t1202 to generate the subject frame image at the time t1202.

Figure 12:
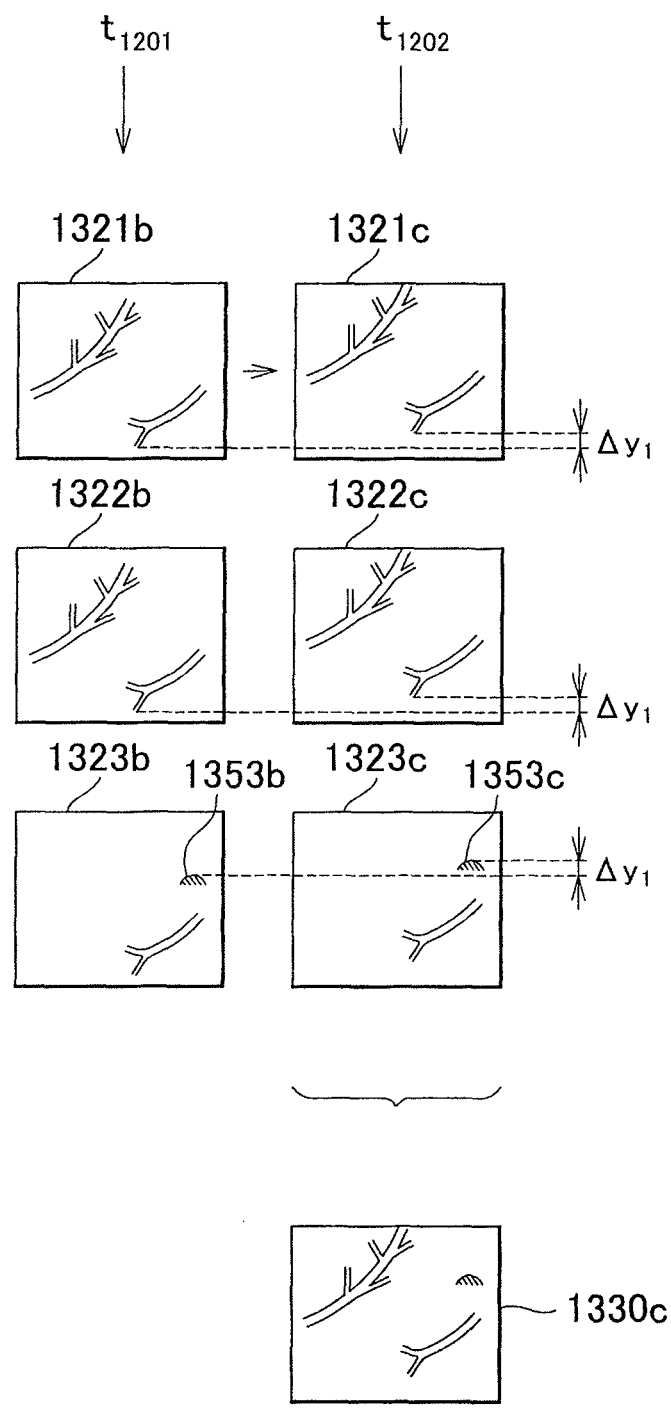
FIG. 12 shows an example of the generation of a subject frame image in which the movement is corrected.

FIGS. 12 and 13 are used to describe the function and configuration of the image processing section 140 for correcting the effect the movement mentioned above on the subject frame images, and this description focuses on the operation of the movement identifying section 710 and the subject image generating section 720. The frame images 1321b, 1322b, 1323b are frame images of the red signal, the green signal, and the blue signal, respectively, at the time t1201. The frame image 1323c is the frame image of the blue signal from the plurality of third light receiving elements 136 at the time t1202.

The movement identifying section 710 identifies the movement based on the content of the frame image 1323b and the frame image 1323c. More specifically, the movement identifying section 710 extracts images of the same subject from the frame image 1323b and the frame image 1323c. In the example of FIG. 12, the movement identifying section 710 extracts the subject images 1353b and 1353c from the frame image 1323b and the frame image 1323c, respectively.

The movement identifying section 710 calculates the difference in position between the subject image 1353b and the subject image 1353c. In FIG. 12, for ease of explanation, the position difference exists in the y-direction of the image so that the movement identifying section 710 calculates a positional difference $\Delta y1$ indicating the positional difference between the subject image 1353b and the subject image 1353c.

The subject image generating section 720 generates the frame image 1321c by shifting the frame image 1321b in the y-direction by an amount corresponding to the calculated positional difference $\Delta y1$. The subject image generating section 720 generates the frame image 1322c by shifting the frame image 1322b in the y-direction by an amount corresponding to the calculated positional difference $\Delta y1$. The subject image generating section 720 generates the subject frame image 1330c by combining the frame image 1321c, the frame image 1322c, and the frame image 1323c. Here, combining the images includes a process for multiplexing the red signal showing the frame image 1321c, the blue signal showing the frame image 1322c, and the green signal showing the frame image 1323c, with a prescribed weighting.

The subject image generating section 720 may change the movement correction amount for each image region in the red signal and green signal frame images. For example, if the image capturing direction of the image capturing apparatus 100 is perpendicular to the surface of the subject and moves horizontally in relation to the surface of the subject, the movement amount of the object is the same in every image region. On the other hand, if the image capturing direction of the image capturing apparatus 100 is not perpendicular to the surface of the subject, the movement amount in image regions captured at positions further from the image capturing apparatus 100 might be smaller than the movement amount in image regions captured at positions closer to the image capturing apparatus 100.

In order to calculate the movement correction amount for each image region in the red signal and green signal frame images, the subject image generating section 720 can calculate the movement correction amount based on the position of an image region and a positional relationship between the surface of the subject and the image capturing apparatus 100, if this positional relationship is known in advance or can be estimated. The subject image generating section 720 may calculate the movement correction amount for the red signal and green signal frame images based on a control value that manipulates the image capturing apparatus 100 to cause a change over time in the image. The control value may be a value that controls the position or orientation of the image capturing apparatus 100, a value that controls the zoom of the image capturing apparatus 100, or the like.

As another example, the movement identifying section 710 may calculate the movement of the subject image in each image region. The subject image generating section 720 may calculate the movement correction amount for each image region in the frame image based on the movement in each image region.

When identifying the movement in each image region, the movement identifying section 710 may determine which wavelength image is used to identify the movement in each image region. For example, the movement identifying section 710 calculates the contrast of each image region in each image. The movement identifying section 710 may then give priority to selecting the image of the wavelength for which the highest contrast was calculated and use this image for the corresponding image region. The movement identifying section 710 uses the plurality of selected frame images to identify the movement.

As described in relation to FIG. 12, the movement identifying section 710 identifies the amount of movement of a subject image between a frame image at a first timing and a frame image at a second timing, based on the frame image resulting from the light received by the third light receiving elements 136 at the first timing and the frame image resulting from the light received by the third light receiving elements 136 at the second timing. The subject image generating section 720 generates the subject frame image at the second timing based on the light received by the first light receiving elements 132 at the first timing, the light received by the second light receiving elements 134 at the second timing, and the movement of the subject image.

FIG. 13 shows another example of the generation of a subject frame image in which the movement is corrected. In the examples in FIG. 13, the movement identifying section 710 identifies the movement using the frame image 1421a of the red signal obtained at the time t1200 and the frame image 1421b of the red signal obtained at the time t1201. In the same manner as the method described in relation to FIG. 12, the movement identifying section 710 extracts subject images showing the same subject from the frame image 1421a and the frame image 1421b. In FIG. 13, the movement identifying section 710 extracts the subject image 1451a and the subject image 1451b from the frame image 1421a and the frame image 1421b, respectively.

The movement identifying section 710 calculates the positional difference between the subject image 1451a and the subject image 1451b. In FIG. 13, for ease of explanation, the position difference exists in the y-direction of the image so that the movement identifying section 710 calculates the positional difference $\Delta y2$ indicating the positional difference between the subject image 1451a and the subject image 1451b. In the same manner as described in relation to FIG. 12, the subject image generating section 720 generates the frame image 1421c by shifting the frame image 1421b in the y-direction by an amount corresponding to the calculated positional difference $\Delta y2$. In the same way, the subject image generating section 720 generates the frame image 1422c by shifting the frame image 1422b in the y-direction by an amount corresponding to the calculated positional difference $\Delta y2$. The subject image generating section 720 generates the subject frame image 1430c by combining the frame image 1421c, the frame image 1422c, and the frame image 1423c, which is the green signal frame image from the third light receiving elements 136 at the time t1202.

The above example uses the frame image 1421a and the frame image 1421b to identify the movement, but the movement identifying section 710 may instead identify the movement using the frame image 1421b and the red signal frame image obtained at the time t1203. In this way, the movement identifying section 710 may identify the movement based on the frame images obtained at a plurality of timings before and after the time t1201, which is the timing at which the red signal frame image in which the movement is corrected is generated. If it is acceptable for the display of the subject frame image to be somewhat delayed, the movement identifying section 710 can more accurately identify the movement by also using images at later timings.

In the above description, the frame image 1422b is corrected based on the movement identified using the frame image 1421a and the frame image 1421b, but the movement identifying section 710 may instead identify the movement using the frame image 1422a and the frame image 1422b. The subject image generating section 720 may then shift the frame image 1422b using the identified movement to generate the frame image 1422c.

The decision concerning which image's wavelength the movement identifying section 710 uses to identify the movement can be decided based on the contrast of the captured image. For example, the movement identifying section 710 can prioritize the use of the frame image having the highest contrast for identifying the movement. If an object with a minute structure is used as the object for identifying the movement, i.e. it is clear that the object has a very fine surface structure, using the blue signal frame images might enable more accurate movement identification. If an object with an uneven structure is used for identifying the movement, i.e. it is clear that the object has a bumpy surface structure, using the red signal frame images might enable more accurate movement identification.

As described in relation to FIG. 13, the movement identifying section 710 identifies the movement of a subject image between frame images obtained at a plurality of timings, based on a plurality of frame images resulting from the light in the first wavelength region received by the first light receiving elements 132 at a plurality of timings that include the first timings but not the second timings. The subject image generating section 720 generates a subject frame image at a second timing based on the light received by the first light receiving elements 132 at the first timings, the light received by the second light receiving elements 134 at the first timing, the light received by the third light receiving elements 136 at the second timing, and the movement of the object. FIGS. 12 and 13 described an exemplary movement identification process in which the movement identifying section 710 identifies the movement based on frame images captured at two different timings, but the movement identifying section may identify the movement based on frame images captured at three or more different timings.

Figure 14:
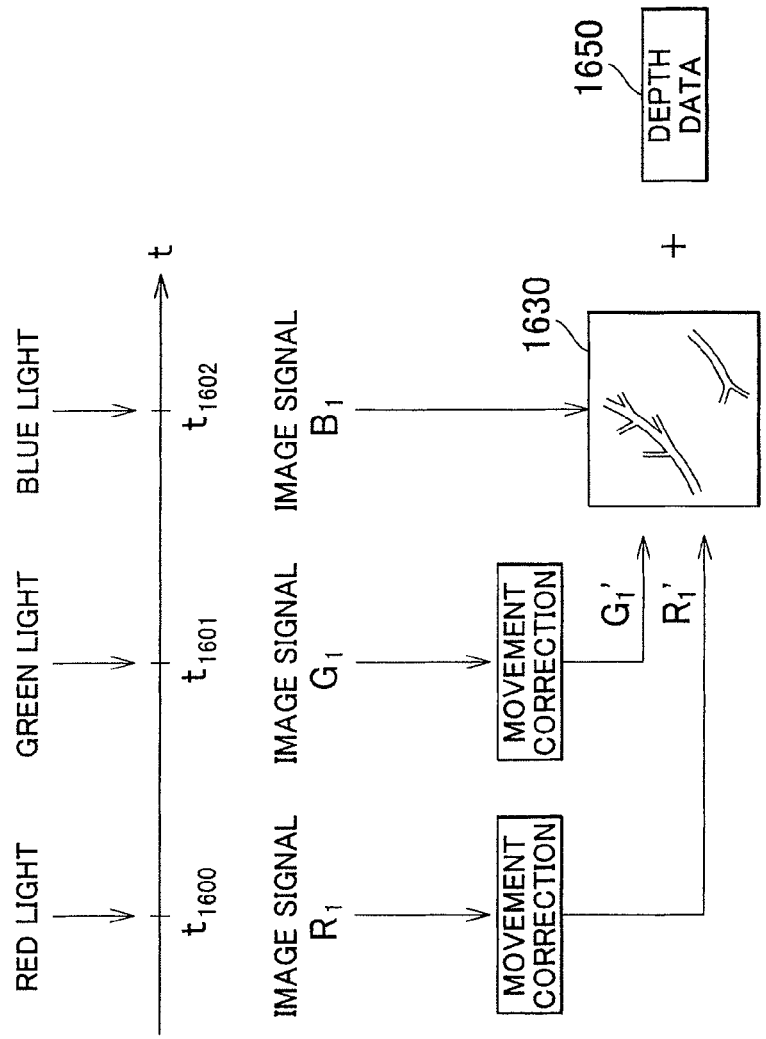
FIG. 14 shows another exemplary emission pattern of the light from the light emitting section 114.

FIG. 14 shows another exemplary emission pattern of light from the light emitting section 114. Here, the filters described above are not provided, so that each light receiving element receives light in substantially the same wavelength region. In this configuration, the light emitting section 114 may emit light in each component included in the viewing light at timed intervals. More specifically, at the times t1600, t1601, and t1602, the light emitting section 114 respectively emits red light, green light, and blue light.

The subject image generating section 720 generates an image signal R1' in which the movement is corrected, by correcting the movement between the time t1600 and the time t1602 in an image signal R1 obtained from all of the light receiving elements at the timing t1600. The subject image generating section 720 generates an image signal G1' in which the movement is corrected, by correcting the movement between the time t1601 and the time t1602 in an image signal G1 obtained from all of the light receiving elements at the timing t1601. The process performed by the movement identifying section 710 to identify the movement between each timing involves identifying the movement based on the image signals obtained from each light receiving element at a plurality of different timings, as described in FIGS. 11 to 13, and therefore further description is not provided.

The subject image generating section 720 can then generate the subject frame image 1630 that is expected to be obtained at the time t1602 by multiplexing the corrected image signal R1', the corrected image signal G1', and an image signal B1 obtained from all of the light receiving elements at the time t1602. In this way, even if each color of light included in the white light is emitted at different times, the image capturing apparatus 100 can generate a subject frame image in which the movement is corrected.

The reflectance calculating section 142 calculates the reflectance in each wavelength region for each image region by using the corrected image signal R1' and the corrected image signal G1'. The depth identifying section 144 calculates the depth data 1650 by identifying the depth of the object for each region, based on the reflectance calculated for each wavelength region. In this way, when red light and green light are emitted sequentially, the depth identifying section 144 can identify the depth of an object using image signals corrected according to the identified movement.

In this way, the movement identifying section 710 can identify the movement of the subject between the sequential emission of light in the first wavelength region and light in the second wavelength region by the light emitting section 114. The reflectance calculating section 142 can calculate the first reflectance and the second reflectance for which the position shift caused by the movement of the subject is corrected, based on the movement identified by the movement identifying section 710. In this way, the image capturing apparatus 100 can more accurately identify the depth of an object.

FIG. 14 is used to describe an example in which each color of light in the white light is emitted sequentially and the depth is identified based on the reflectance of each color of light, but, as described in relation to FIG. 10, the light emitting section 114 may further emit measurement light for measuring the depth at a different timing. The movement identification and correction for an image signal obtained from such a light emission pattern can be performed in the same manner as described above, and therefore further description is not provided.

The light emitting section 114 that sequentially emits each color light in the viewing light may be configured to include a light source that emits the viewing light and a filter that selectively passes each color light in sequence. This filter may be a filter that can control the passed wavelength region over time, such as a liquid crystal filter, or a rotating filter having a plurality of filter regions that selectively pass each color light in sequence. The method of controlling the wavelength of the light irradiating the subject by using such a filter can also be used when radiating the viewing light and the measurement light at different times, as described in relation to FIG. 10 and the like.

The light emitting section 114 can emit the viewing light and the measurement light at different times or sequentially emit each color light by controlling a plurality of light emitting elements that emit light in different wavelength regions. The light emitting elements that emit the viewing light may be semiconductor elements such as LEDs. The light emitting elements that emit the light for measuring depth may be semiconductor elements that emit light in a relatively narrow wavelength region, such as semiconductor lasers. The light emitting section 114 can emit the viewing light and the measurement light at different times or sequentially emit each color light by controlling the emission intensity of each plurality of light emitting elements at each timing.

If the image capturing apparatus 100 is an endoscope, the light emitting elements may be provided on the tip of the scope. These light emitting elements may emit light by electrical excitation or by optical excitation. Such light emitting elements may be fluorescent bodies or the like. In the case of optical excitation, the light emitting section 114 may include the light emitting elements and an exciting section that emits light for exciting the light emitting elements. Here, the light emitting elements may emit light in different spectrums in response to the wavelength of the excitation light. In this case, the light emitting section 114 can control the spectrum of the radiated light by controlling the wavelength of the excitation light emitted from the exciting section at each timing. Instead, the same excitation light may be used to cause each light emitting element emit light in a different spectrum.

Figure 15:
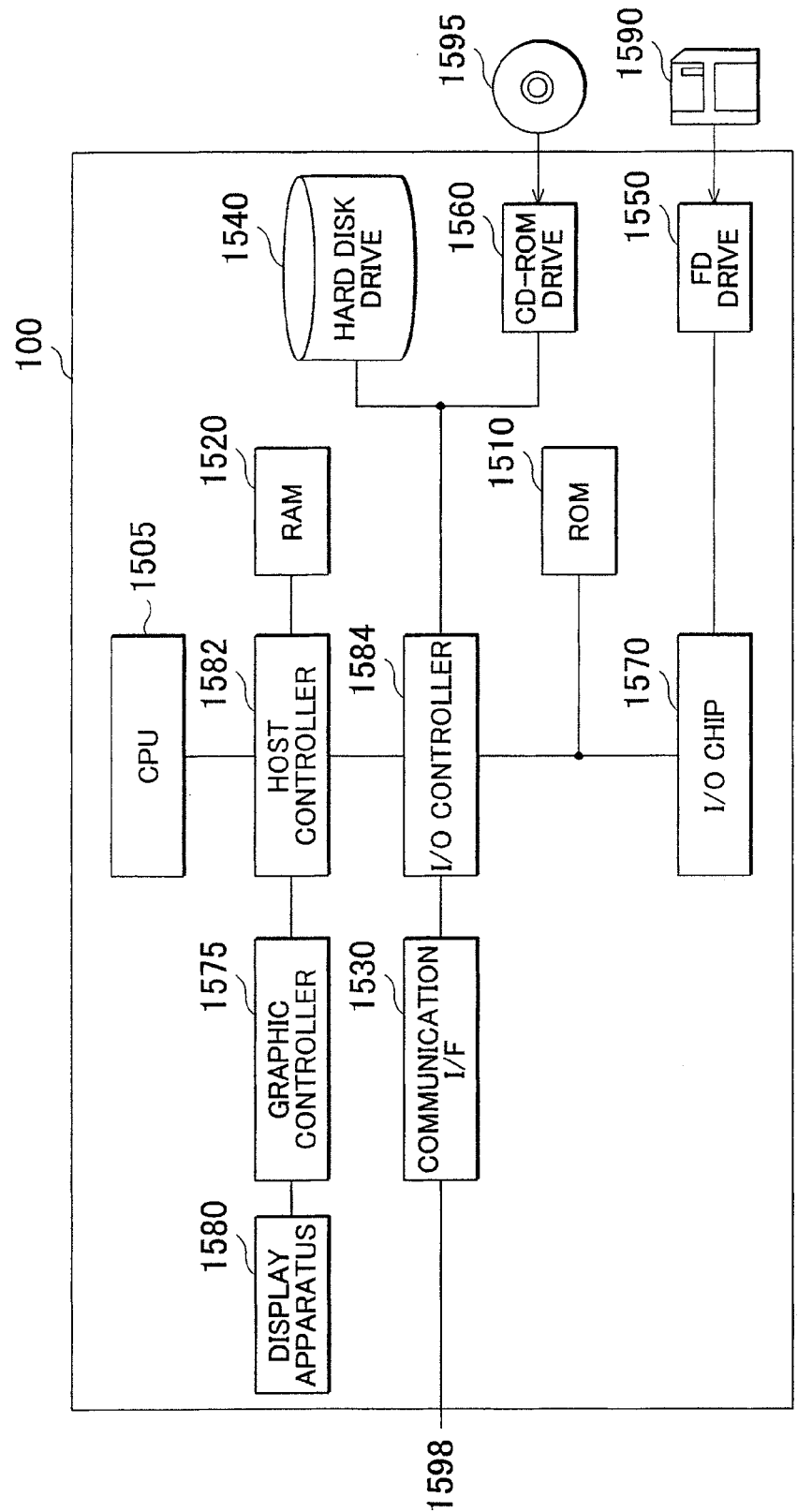
FIG. 15 shows an exemplary hardware configuration of the image capturing apparatus 100.

FIG. 15 shows an exemplary hardware configuration of the image capturing apparatus 100. The function of the image capturing apparatus 100 can be realized by an electronic information processing apparatus such as a computer. The image capturing apparatus 100 according to the present embodiment is provided with a CPU peripheral section that includes a CPU 1505, a RAM 1520, a graphic controller 1575, and a display apparatus 1580 connected to each other by a host controller 1582; an input/output section that includes a communication interface 1530, a hard disk drive 1540, and a CD-ROM drive 1560, all of which are connected to the host controller 1582 by an input/output controller 1584; and a legacy input/output section that includes a ROM 1510, a flexible disk drive 1550, and an input/output chip 1570, all of which are connected to the input/output controller 1584.

The host controller 1582 is connected to the RAM 1520 and is also connected to the CPU 1505 and graphic controller 1575 accessing the RAM 1520 at a high transfer rate. The CPU 1505 operates to control each section based on programs stored in the ROM 1510 and the RAM 1520. The graphic controller 1575 acquires image data generated by the CPU 1505 or the like on a frame buffer disposed inside the RAM 1520 and displays the image data in the display apparatus 1580. In addition, the graphic controller 1575 may internally include the frame buffer storing the image data generated by the CPU 1505 or the like.

The input/output controller 1584 connects the hard disk drive 1540, the communication interface 1530 serving as a relatively high speed input/output apparatus, and the CD-ROM drive 1560 to the host controller 1582. The communication interface 1530 communicates with other apparatuses via the network. The hard disk drive 1540 stores the programs used by the CPU 1505 in the image capturing apparatus 100. The CD-ROM drive 1560 reads the programs and data from a CD-ROM 1595 and provides the read information to the hard disk drive 1540 via the RAM 1520.

Furthermore, the input/output controller 1584 is connected to the ROM 1510, and is also connected to the flexible disk drive 1550 and the input/output chip 1570 serving as a relatively high speed input/output apparatus. The ROM 1510 stores a boot program performed when the image capturing apparatus 100 starts up, a program relying on the hardware of the image capturing apparatus 100, and the like. The flexible disk drive 1550 reads programs or data from a flexible disk 1590 and supplies the read information to the hard disk drive 1540 and via the RAM 1520. The input/output chip 1570 connects the flexible disk drive 1550 to each of the input/output apparatuses via, for example, a parallel port, a serial port, a keyboard port, a mouse port, or the like.

The programs provided to the hard disk 1540 via the RAM 1520 are stored on a recording medium such as the flexible disk 1590, the CD-ROM 1595, or an IC card and are provided by the user. The programs stored on the recording medium may be compressed or uncompressed. The programs are read from the recording medium, installed on the hard disk drive 1540 in the image capturing apparatus 100 via the RAM 1520, and are performed by the CPU 1505. The programs executed by the CPU 1505 cause the image capturing apparatus 100 to function as each component of the image capturing apparatus 100 described in relation to FIGS. 1 to 14.

The programs and modules shown above may also be stored in an external storage medium. The flexible disk 1590, the CD-ROM 1595, an optical storage medium such as a DVD or CD, a magneto-optical storage medium, a tape medium, a semiconductor memory such as an IC card, or the like can be used as the storage medium. Furthermore, a storage apparatus such as a hard disk or RAM that is provided with a server system connected to the Internet or a specialized communication network may be used to provide the programs to the image capturing apparatus 100 via the network.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

What is claimed is:

1. An image capturing apparatus comprising:
a light emitting section that emits light to a subject;
a light receiving section that receives light in a first wavelength region, light in a second wavelength region, and light in a third wavelength region from the subject, the second wavelength region being different from the first wavelength region;
a reflectance calculating processing unit configured to calculate a first reflectance of light in the first wavelength region from the subject and a second reflectance of light in the second wavelength region from the subject, based on the light emitted by the light emitting section and the light received by the light receiving section;
a depth identifying processing unit configured to calculate a depth, from a surface of the subject, of an object inside the subject that is included in an image resulting from the light received by the light receiving section, based on the first reflectance and the second reflectance;
a movement identifying processing unit configured to identify movement of the subject, the movement identifying processing unit determining which wavelength region of the first, second and third wavelength regions is used to identify the movement of the subject in each image region based on a contrast of a captured image taken with at least one of the first, second and third wavelength regions,
wherein the reflectance calculating processing unit calculates the first reflectance and the second reflectance from the light in the first wavelength region and the light in the second wavelength region, respectively, for which a positional shift caused by the movement of the subject is corrected using the movement identified by the movement identifying processing unit based on the light in the wavelength region determined by the movement identifying processing unit to provide a movement-corrected image signal; and
a display configured to display a corrected image based on the movement-corrected image signal.

2. The image capturing apparatus according to claim 1, further comprising a depth storage memory that stores information concerning the depth at which the object exists inside the subject, in association with a difference or ratio between the first reflectance and the second reflectance, wherein
the depth identifying processing unit identifies a depth stored in the depth storage memory in association with the difference or ratio between the first reflectance and the second reflectance.

3. The image capturing apparatus according to claim 2, wherein
the light receiving section receives light in the first wavelength region and light in the second wavelength region, which have different degrees of dependency on the reflectance of the subject according to the depth of the object from the surface of the subject.

4. The image capturing apparatus according to claim 2, wherein
the light receiving section includes a plurality of light receiving elements,
the reflectance calculating processing unit calculates the first reflectance and the second reflectance for each of a plurality of partial regions, which each correspond to a prescribed number of light receiving elements, and the depth identifying processing unit identifies the depth of the object from the surface of the subject for each of the plurality of partial regions.

5. The image capturing apparatus according to claim 1, wherein the light emitting section emits light that includes light in the first wavelength region and light in the second wavelength region, and the light receiving section includes a plurality of first light receiving elements that receive light in the first wavelength region and a plurality of second light receiving elements that receive light in the second wavelength region.

6. The image capturing apparatus according to claim 1, wherein the light emitting section sequentially emits light in the first wavelength region and light in the second wavelength region, and the light receiving section sequentially receives light in the first wavelength region and light in the second wavelength region.

7. The image capturing apparatus according to claim 6, wherein the movement identifying processing unit identifies movement of the subject between the sequential emission of light in the first wavelength region and light in the second wavelength region by the light emitting section.

8. The image capturing apparatus according to claim 1, wherein the light receiving section receives light in a red light wavelength region as the light in the first wavelength region and light in a green light wavelength region as the light in the second wavelength region.

9. The image capturing apparatus according to claim 1, wherein the movement identifying processing unit identifies the movement of the subject between a first timing and a second timing based on the light in the wavelength region determined by the movement identifying processing unit received at the first timing and the light in the wavelength region determined by the movement identifying section received at the second timing; and the reflectance calculating processing unit calculates the first reflectance and the second reflectance at the second timing from the light in the first wavelength region received at the first timing and the light in the second wavelength region received at the first timing, respectively, for which a positional shift caused by the movement of the subject is corrected based on the movement of the subject identified by the movement identifying processing unit.

10. An image capturing method comprising:

providing a light emitting section that emits light to a subject;

providing a light receiving section that receives light in a first wavelength region, light in a second wavelength region, and light in a third wavelength region from the subject, the second wavelength region being different from the first wavelength region;

calculating, using a processing unit, a first reflectance of light in the first wavelength region from the subject and a second reflectance of light in the second wavelength region from the subject, based on the light emitted by the light emitting section and the light received by the light receiving section;

calculating, using a processing unit, a depth, from a surface of the subject, of an object inside the subject that is included in an image resulting from the light received by the light receiving section, based on the first reflectance and the second reflectance, identifying movement of the subject, the movement identifying determining which wavelength region of the first, second and third wavelength regions is used to identify the movement of the subject in each image region based on a contrast of a captured image taken with at least one of the first, second and third wavelength regions, wherein the calculation of the first reflectance and the second reflectance from the light in the first wavelength region and the light in the second wavelength region, respectively, for which a positional shift caused by the movement of the subject is corrected using the movement identified based on the light in the wavelength region determined by the movement identifying step provides a movement-corrected image signal; and displaying to a display unit a corrected image based on the moves ent-corrected image signal.

11. A non-transitory computer readable medium storing thereon a program for use by an image capturing apparatus, wherein the program comprises instructions for performing steps, said steps comprising:

causing a light emitting device to emit light to a subject; and causing a light receiving device to receive light in a first wavelength region, light in a second wavelength region, and light in a third wavelength region from the subject, the second wavelength region being different from the first wavelength region, and the program causing the image capturing apparatus to perform operations including:

calculating a first reflectance of light in the first wavelength region from the subject and a second reflectance of light in the second wavelength region from the subject, based on the light emitted by the light emitting section and the light received by the light receiving section;

calculating a depth, from a surface of the subject, of an object inside the subject that is included in an image resulting from the light received by the light receiving section, based on the first reflectance and the second reflectance, identifying movement of the subject, the movement identifying determining which wavelength region of the first, second and third wavelength regions is used to identify the movement of the subject in each image region based on a contrast of a captured image taken with at least one of the first, second and third wavelength regions, wherein the calculation of the first reflectance and the second reflectance from the light in the first wavelength region and the light in the second wavelength region, respectively, for which a positional shift caused by the movement of the subject is corrected using the movement identified based on the light in the wavelength region determined by the movement identifying step to provide a movement-corrected image signal; and displaying a corrected image using the movement-corrected image signal.

* * * * *